United States Patent [19]
Anderson

[11] Patent Number: 6,007,517
[45] Date of Patent: Dec. 28, 1999

[54] RAPID EXCHANGE/PERFUSION ANGIOPLASTY CATHETER

[76] Inventor: R. David Anderson, 53230 Oakbrook Dr., Durham, N.C. 27718

[21] Appl. No.: 08/699,559

[22] Filed: Aug. 19, 1996

[51] Int. Cl.[6] .................................................. A61M 29/00
[52] U.S. Cl. ............................................. 604/96; 606/194
[58] Field of Search ...................... 604/96–102; 606/192, 606/194

[56] References Cited

U.S. PATENT DOCUMENTS

| | | |
|---|---|---|
| 4,581,017 | 4/1986 | Sahota . |
| 4,601,713 | 7/1986 | Fuqua ........................ 604/280 |
| 4,762,129 | 8/1988 | Bonzel . |
| 4,771,777 | 9/1988 | Horzewski .............................. 128/344 |
| 4,790,315 | 12/1988 | Mueller, Jr. et al. . |
| 4,819,751 | 4/1989 | Shimada et al. . |
| 4,850,969 | 7/1989 | Jackson . |
| 4,909,252 | 3/1990 | Goldberger . |
| 4,909,781 | 3/1990 | Husted . |
| 4,944,745 | 7/1990 | Sogard et al. . |
| 4,983,167 | 1/1991 | Sahota . |
| 4,988,356 | 1/1991 | Crittenden et al. . |
| 4,994,033 | 2/1991 | Shockey et al. ......................... 604/101 |
| 5,040,548 | 8/1991 | Yock . |
| 5,046,503 | 9/1991 | Schneiderman . |
| 5,049,131 | 9/1991 | Deuss ........................ 604/96 |
| 5,061,273 | 10/1991 | Yock . |
| 5,078,685 | 1/1992 | Colliver . |
| 5,102,403 | 4/1992 | Alt ........................ 604/280 |
| 5,108,370 | 4/1992 | Walinsky . |
| 5,116,318 | 5/1992 | Hillstead . |
| 5,135,535 | 8/1992 | Kramer . |
| 5,147,377 | 9/1992 | Sahota . |
| 5,154,725 | 10/1992 | Leopold . |
| 5,156,594 | 10/1992 | Keith . |
| 5,158,540 | 10/1992 | Wijay et al. . |
| 5,171,222 | 12/1992 | Euteneuer et al. . |
| 5,180,367 | 1/1993 | Kontos et al. . |
| 5,205,822 | 4/1993 | Johnson et al. . |
| 5,232,445 | 8/1993 | Bonzel . |
| 5,267,958 | 12/1993 | Buchbinder et al. . |
| 5,284,473 | 2/1994 | Calabria . |
| 5,295,959 | 3/1994 | Gurbel et al. . |
| 5,295,995 | 3/1994 | Kleiman . |
| 5,308,356 | 5/1994 | Blackshear, Jr. et al. . |
| 5,318,535 | 6/1994 | Miraki . |
| 5,324,269 | 6/1994 | Miraki . |
| 5,336,184 | 8/1994 | Teirstein . |
| 5,342,297 | 8/1994 | Jang . |
| 5,346,505 | 9/1994 | Leopold . |
| 5,370,617 | 12/1994 | Sahota . |
| 5,378,237 | 1/1995 | Boussignac et al. ...................... 604/96 |
| 5,383,856 | 1/1995 | Bersin . |
| 5,383,890 | 1/1995 | Miraki et al. . |
| 5,395,333 | 3/1995 | Brill . |
| 5,395,353 | 3/1995 | Scribner . |
| 5,403,274 | 4/1995 | Cannon . |
| 5,409,458 | 4/1995 | Khairkhahan et al. . |
| 5,411,478 | 5/1995 | Stillabower . |

(List continued on next page.)

*Primary Examiner*—Wynn Wood Coggins
*Assistant Examiner*—Deborah Blyveis
*Attorney, Agent, or Firm*—Millen, White, Zelano & Branigan, P.C.

[57] ABSTRACT

A balloon dilatation catheter for the performance of percutaneous transluminal angioplasty of the coronary or other arteries is provided. The design of the catheter is such that in the deflated or collapsed configuration it defines a very low profile device allowing its delivery to a broader range of blood vessels within the body and the ability to be placed across very severe blockages in any given vascular space. The catheter in its inflated state has an outer surface that resembles standard angioplasty balloons. It has an interior channel through which a guidewire can pass to enable rapid exchange and per-fusion. Optionally, it can also have a second channel in the interior for perfusion. The channels within the balloon are asymmetrically placed (with respect to the shaft), when viewed in cross section, and are comprised, e.g., of balloon material, either of standard or increased thickness, or in addition may be reinforced by an additional supplemental cylindrical structure of a collapsible or non-collapsible nature.

12 Claims, 11 Drawing Sheets

U.S. PATENT DOCUMENTS

| | | |
|---|---|---|
| 5,425,709 | 6/1995 | Gambale . |
| 5,425,714 | 6/1995 | Johnson et al. . |
| 5,433,706 | 7/1995 | Abiuso . |
| 5,470,314 | 11/1995 | Walinsky . |
| 5,472,425 | 12/1995 | Teirstein . |
| 5,484,411 | 1/1996 | Inderbitzen et al. . |
| 5,484,412 | 1/1996 | Pierpont . |
| 5,489,271 | 2/1996 | Anderson ................................ 604/102 |
| B1 4,581,017 | 5/1994 | Sahota . |

RAPID EXCHANGE/PERFUSION ANGIOPLASTY CATHETER

BACKGROUND

This invention involves a device suitable for angioplasty that allows its use as a single operator exchange catheter (rapid exchange) and optionally also allows the continued flow of blood distal to the catheter throughout the balloon inflation period of the procedure.

The objective of the first angioplasty procedure described by Grundzig in 1977 was to be able to relieve the blockages that can occur within coronary arteries blood vessels that feed the heart muscle). These blockages (or stenoses) occur most commonly from atherosclerotic disease causing a lipid laden plaque to develop on the inner surface of a blood vessel wall. Stenoses may also arise from other processes such as radiation injury or diseases such as fibromuscular dysplasia. The procedure was designed to relieve these obstructions and restore blood flow by the use of a distensible balloon on the distal end of a catheter shaft. Once placed across an obstruction within the vascular lumen, inflation of the balloon causes distention of the inner lumen of the blood vessel and a decrease in the blockage such that when the balloon is deflated the result is a larger lumen with a smaller stenosis. The angioplasty procedure has become commonly used in medical practice. It is performed via a percutaneous approach and therefore avoids the need for surgery. Percutaneous angioplasty is most frequently used in the arteries of the coronary, renal, and the peripheral circulations of the human body; however, its use in the cerebral and other vascular beds is also possible.

The standard angioplasty procedure begins with access to the cardiovascular space under local anesthetic and placement of a guiding catheter to the ostium of a coronary artery. The guiding catheter allows the introduction of a radio-opaque dye into the site for visualization of any stenoses. This visualization permits appropriate sizing of a balloon dilatation catheter. Subsequent to this, a guidewire is placed through the guiding catheter up to and across the vascular stenosis. An angioplasty catheter is then advanced over the guidewire, but still within the guiding catheter, until the balloon on the distal tip of the catheter is across the area of stenosis. Inflation of the balloon, also with radio-opaque contrast, causes distention of the vascular lumen and stenosis, and then deflation leaves a larger lumen with compressed plaque, thrombus, fibrous and/or other tissue. The net result is to increase the cross sectional area or lumen of the blood vessel and ultimately to improve the amount of blood flow present at the termination of the procedure.

The angioplasty procedure as currently practiced often requires the use of more than one catheter. The placement of a standard angioplasty catheter over a guidewire requires that a length of wire protrude outside the patient that is longer than the catheter itself. This allows the operator to always be able to maintain contact with the external guidewire while advancing the balloon into the patient, to be able to maintain the distal guidewire across the lesion of interest and to maintain a grip on the guidewire during catheter removal. Having to reinsert a guidewire takes extra time and increases the risk of the procedure. The length of wire required to perform this procedure can include as much as 150 to 200 cm protruding from a patient. This length must be kept sterile throughout the procedure and usually requires a second person in sterile scrub to hold it and maintain it within the sterile field.

Catheter systems have been designed that allow the advancement or removal of an angioplasty catheter over a guidewire by a single operator while not losing the ability to hold the guidewire, i.e., so called rapid exchange catheters. The use of a rapid exchange system reduces guidewire length, decreases the risk of a break in sterility and obviates the need for an assistant during the procedure. Additionally, having to advance a conventional catheter along the entire length of a guidewire imposes significant friction, taxing the operator's ability to push the catheter. This friction also detracts from the physician's sense of tactile response which is important to the success of the procedure.

Current rapid exchange catheters have set distances from the distal tip of the shaft where the guidewire exits the shaft through the proximal exit site. These distances are long enough that they can lead to difficulty for the physician in having to transfer his hold on the guidewire to the angioplasty catheter, risking movement of the guidewire. Other prior art systems place the port for the guidewire on the exterior surface of the balloon such that, in its inflated state, the profile of the balloon-guidewire combination would not allow symmetric deployment of an intracoronary stent. The importance of adequate apposition of stent struts to the vessel wall at deployment is now known to be of great importance in reducing the rates of acute vessel closure and follow-up restenosis. For rapid exchange catheters see U.S. Pat. No. 4,762,129, and U.S. Pat. No. 5,061,273.

All of these catheters have undesirable characteristics of one sort or another. There remains a need for an improved rapid exchange catheter, e.g., having as low a profile as possible, requiring as short a length of guidewire outside the patient as possible and permitting symmetrical deployment of stents when needed.

Another problem associated with the use of standard angioplasty balloons is their inability to permit the distal perfusion of the blood vessel when the balloon is inflated. Thus, there exist potential complications from the resulting cessation of blood flow within the vascular space. These complications are the direct result of balloon inflation and increase as the time without blood flow lengthens. The result can be myocardial ischemia (inadequate blood flow to the heart muscle) manifested by the patient having chest pain, arrhythmias, myocardial infarction or even death. In addition, the use of standard angioplasty balloons is associated with arterial injury. The denuding of the vascular endothelium allows the release of mediators of the inflammatory response which causes platelet activation leading to thrombus formation. This is associated with a 2–5% incidence of abrupt closure of the vessel which can also lead to myocardial infarction, the need for emergency bypass surgery or death.

Perfusion angioplasty dilatation catheters are designed to permit blood flow distal to the inflated balloon for the purpose of limiting these potential complications. In a randomized trial of a perfusion balloon compared with a non-perfusion balloon in the treatment of patients undergoing elective angioplasty, patients treated with prolonged inflations using the perfusion balloon had a higher procedural success rate and a lower rate of arterial injury than those treated with standard balloons and shorter inflation times.

Another long term issue that plagues the angioplasty procedure is the problem of restenosis at the site of balloon dilatation that occurs within six months in 30 to 50% of patients. While the use of a perfusion angioplasty catheter has not been shown to reduce the rate of restenosis at six months of follow-up, recent experiments with the use of intracoronary irradiation show considerable promise in reducing restenosis rates. In both experimental animals and humans, intracoronary irradiation has decreased the follow-up restenosis rate. The delivery of radioactive seeds on the end of a guidewire appears to require the use of a balloon angioplasty catheter for the purpose of centering the seeds within the vascular space for symmetric radiation delivery. A perfusion catheter is also required to provide distal perfusion while allowing the seeds to remain in place for 20 to 30 minutes, the estimated time required to deliver the appropriate radioactive dose in situ.

Many non-perfusion angioplasty catheters have been disclosed with their respective methods of construction, preparation and usage. See, e.g., the disclosures of U.S. Pat. No. Reissue 33,166 and U.S. Pat. Nos. 4,169,263, 4,323,071, 4,411,055, 4,571,240, 4,573,470, 4,582,181, 4,597,755, 4,616,653, 4,619,263, 4,638,805, 4,641,654, 4,664,113, 4,692,200, 4,748,982, 4,771,776, 4,771,778, 4,775,371, 4,782,834, 4,790,315 and 4,793,350.

There are also several known perfusion angioplasty catheters. U.S. Pat. No. 4,581,017 represents the only commercially marketed perfusion catheter presently available in the United States. It provides distal coronary perfusion through the central catheter shaft via serial ports just proximal and also distal to the balloon. Blood flow travels through the center of the balloon. The drawbacks of this technology include the need to retract the guidewire for perfusion to occur, as well as the relatively high profile of the device limiting its use in smaller vessels. In addition, blood flow distal to the catheter is limited by the inner diameter of the central shaft and is usually considerably less than normal (e.g., $\leq 40$ ml/min, where normal=80–100 ml/min) in the case of coronary blood flow.

Other perfusion catheters also have been disclosed. See, e.g., U.S. Pat. Nos. 5,078,685, 4,909,252, 5,108,370, 5,470,314, 5,433,706, 5,472,425, 5,295,959, 5,370,617, 4,944,745, 5,425,709, 4,790,315, 5,308,356, 5,383,890, 5,395,333, 5,395,353, 5,284,473, 5,484,412, 4,850,969, 5,378,237, 5,425,714, 5,403,274, 5,158,540, 5,318,535, 4,771,777, 5,046,503, 5,484,411, 5,295,995 and 5,383,856. However, all of these are unsatisfactory in one aspect or another, e.g., manufacturing issues or potential application limitations due to size or other design features.

Therefore, the availability of a perfusion angioplasty catheter that is easy to manufacture, does not require use of a central lumen of the shaft for blood flow and does not increase catheter profile would be advantageous to the interventional cardiology profession.

SUMMARY OF THE INVENTION

The current invention provides an improved catheter which achieves rapid exchange and/or perfusion, simultaneously if desired, while overcoming the mentioned shortcomings, among other things. It achieves these ends by incorporating a channel internalized within the angioplasty balloon but not within the central shaft. Its reduced length reduces the friction of longer rapid exchange channels. It does not increase the overall profile of the device in its deflated state and will allow for symmetric stent delivery. At the same time, this design provides for distal perfusion. If the guidewire is placed through the catheter shaft as usual, the internal balloon channel may be used for blood flow when the balloon is inflated. Even when the wire is placed through the channel for rapid exchange, the same channel can achieve distal perfusion depending on the relative sizes of wire and channel. Alternatively, two or more channels can be designed in the balloon, e.g., one for the wire and one for blood flow. There are no catheters currently disclosed that have the ability to be used as a rapid exchange catheter while providing distal perfusion at the same time.

The present invention thus overcomes the problems of the prior art. It provides a rapid exchange perfusion balloon that has one or more asymmetrically positioned channels (with respect to the central catheter shaft when viewed in cross section) formed longitudinally within the balloon. The exterior surface of the balloon thus has a smooth surface like that of standard angioplasty balloons; hence, it avoids the potential blocking of channels placed on the exterior surface of the balloon in some prior art embodiments. The interior surface (s) of the balloon, whether reinforced or not, provide(s) channel(s) to be used for rapid exchange, the flow of blood distal to the inflated balloon, or both. Where reinforcements or scaffolds are used, they enhance maintenance of channel integrity during higher pressure inflation. The channels may be asymmetrically positioned, as mentioned, parallel and close to the center shaft of the catheter, or they may be formed a greater radial distance from the shaft closer to the exterior surface of the balloon. The catheter and its shaft will have the features needed for operation, e.g., for balloon inflation, a central channel for guidewire placement when only perfusion is to be achieved by use of the channels of this invention, etc. The central shaft of the catheter can also be used for the maintenance of perfusion when the channel is used for guidewire placement, but this design is not preferred.

In the rapid exchange embodiment, the central shaft may in fact be smaller than conventional systems (since the wire doesn't need to pass through it), or it may just be a wire, rod, etc. for rigidity, e.g., a small solid wire shaft, but no shaft in the traditional sense because the guidewire goes through the channel.

Thus, the new designs discussed herein improve upon current perfusion catheter technology. The placement of asymmetric channels within the balloon provides the rapid exchange option and a perfusion option with flows averaging 60–80 ml/min while the device maintains a very low profile. The latter feature permits it to be used in a wide range of situations, e.g., as a method of bailout after procedural complications and also as a primary device in arteries where perfusion balloons could not previously be applied, as well as in conventional situations. This should lead to a decrease in the number of acute procedural complications and ultimately to improved patient care.

Thus, this invention relates to
  a balloon catheter useful for angioplasty, comprising
    an angioplasty balloon having a proximal and a distal end and having a first channel passing through its interior from its proximal to its distal end, and
    a guidewire passing through said first interior channel from said proximal to said distal end of the balloon.

In preferred aspects, the balloon is concentrically mounted on a shaft, solid or having conventional lumens and/or an outer groove per this invention for receiving the guidewire when the balloon is deflated; the channel(s) are reinforced; and/or the balloon comprises a second channel for perfusion when the balloon is inflated in a blood vessel.

In another aspect, this invention relates to a perfusion balloon dilatation catheter, comprising
  a catheter shaft and concentrically mounted on and encircling said shaft, an inflatable dilatation balloon useful for angioplasty comprising
    an inflatable space defined by an outer closed surface which contacts an inner surface of a blood vessel when said balloon is inflated in said blood vessel, and distal and proximal ends along said shaft, said balloon when inflated having at least one walled channel formed in its interior, between said outer surface and said shaft, which extends from said proximal end to said distal end, the wall of said channel comprising a closed surface which is distinct from the surface of said shaft and which has a portion closest to said balloon outer surface and a portion closest to said shaft, whereby when said balloon is inflated in a blood vessel and said outer surface is in contact with the inner surface of said blood vessel, blood flows through said inner channel from the proximal to the distal end of said balloon.

In preferred aspects, the portion of said inner channel wall closest to said balloon outer surface adjoins said balloon outer surface along a line from said balloon proximal end to said distal end. In other aspects, this invention relates to, in a perfusion balloon dilatation catheter comprising a center annular shaft and, mounted thereon, an encircling inflatable balloon surface, an improvement comprising an inner channel in the balloon located between said balloon surface and said shaft, said channel being defined by a surface which is distinct from said shaft and said balloon surface;

such a perfusion balloon dilatation catheter which has a cross section comprising the generally circular surface of said balloon, the inner and outer surfaces of said annular shaft and, located between said centered shaft and said generally circular surface, the surface defining said inner channel;

and in a perfusion balloon dilatation catheter comprising a center annular shaft and, mounted thereon, an encircling inflatable balloon surface, an improvement wherein said balloon surface is folded on itself along a line generally parallel to said shaft and is sealed along said line to create a balloon outer surface and therein a channel made of said balloon surface which is folded on itself.

In any of the foregoing additional aspects, a second balloon channel may be used for passage of a guidewire.

Thus, the device of this invention can function as a rapid exchange catheter, a perfusion catheter or both.

The term "encircling" as used with respect to this invention does not require a shape which is precisely circular. Rather, the expression is meant merely to imply that the balloon outer wall is substantially circular in nature and defines a path around the catheter shaft. Similarly, the expression "substantially circular," when applied to the channel shape, means that the channel need not be circular, although such a shape would be preferred. Rather, the shape of the channel is not critical and can be circular, irregular, elliptical, etc; it is satisfactory that whatever shape the walls of the channel take, the channel remains open when the balloon is inflated sufficiently to allow movement of the guidewire in the rapid exchange embodiment or blood flow in the perfusion embodiment. The term "wall" is not meant to imply any particular structure of the surfaces which define the channel; thus, there can be a single wall where the channel has a curvalinear cross-sectional shape; there can also be one or more walls, e.g., where the cross-sectional shape is more like that of a polygon. Where the term "distinct" is used to describe the channel wall in its relationship to the shaft, it is meant that the shaft itself does not form the inner surface of the channel, e.g., that an additional material forms the inner channel surface. The term "adjoin," as used herein, refers to the fact that the two elements so described are in contact with one another.

Figure 1A:
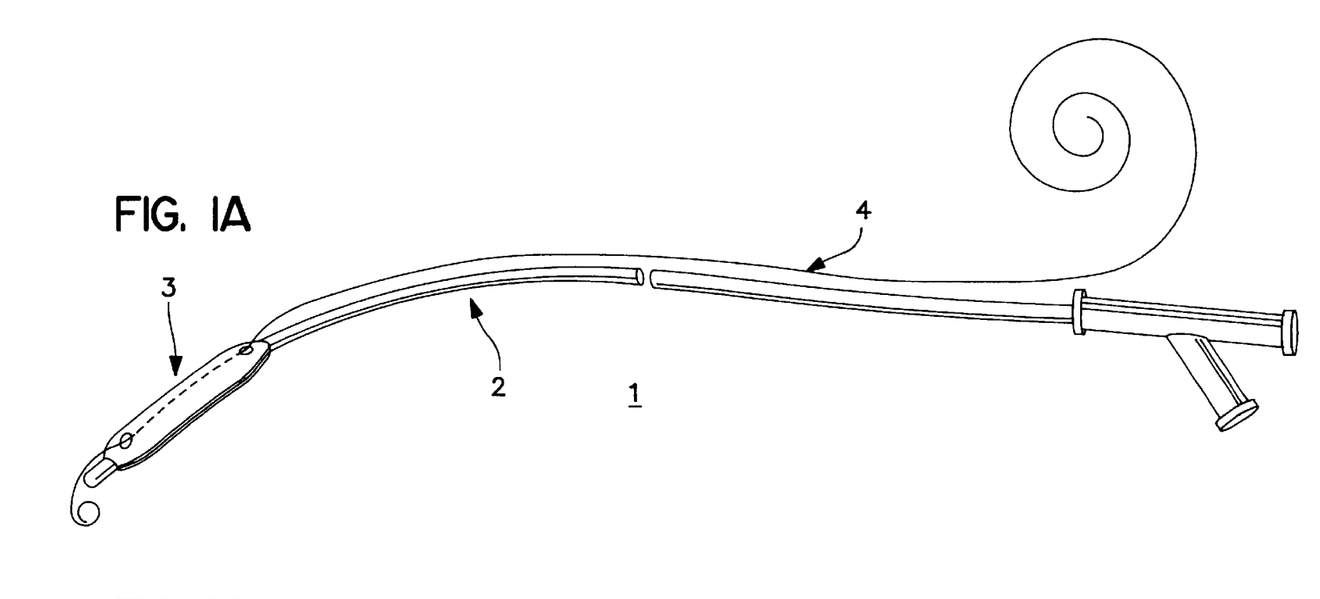
Figure 1B:
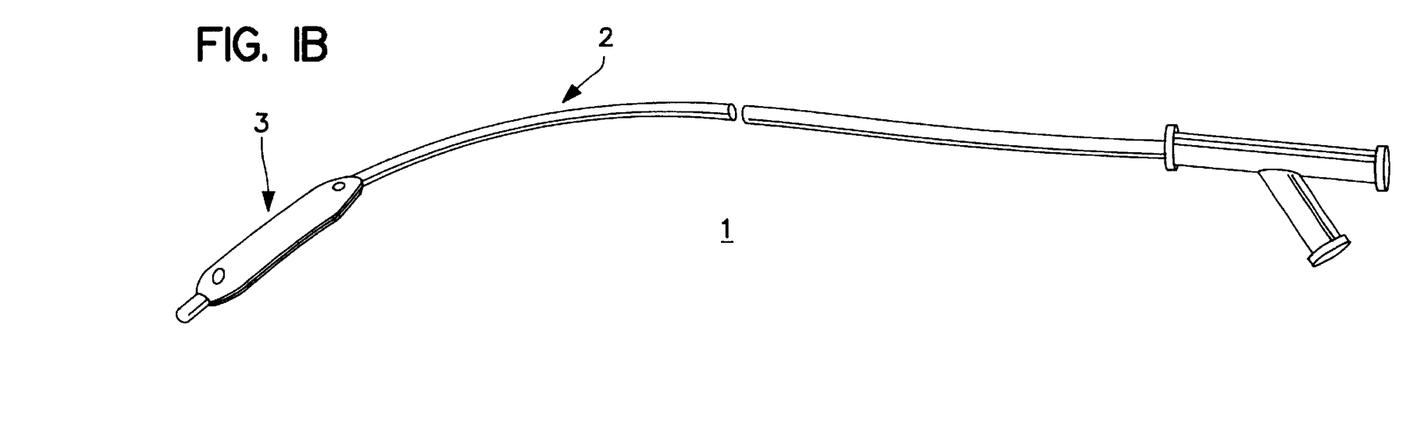
Figure 1C:
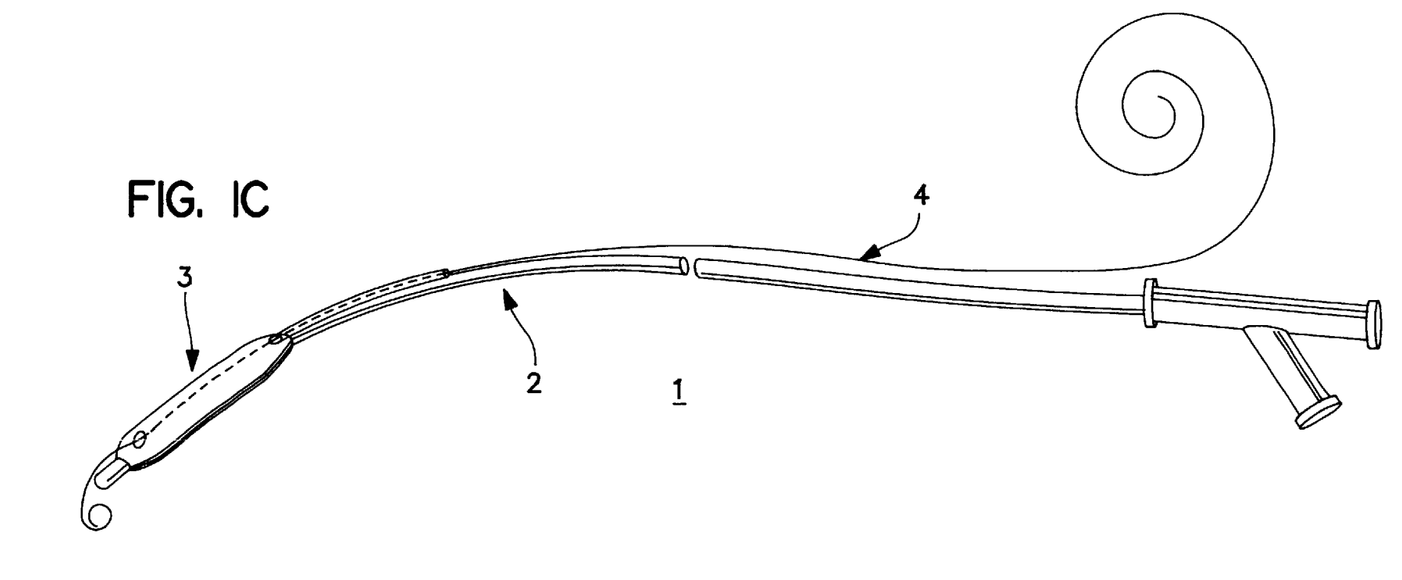

This invention thus relates to a rapid exchange catheter 1 (see "A" Figures) and a perfusion catheter (see "B" Figures) or a combination thereof. The device is comprised of, typically, a catheter shaft 2, and, mounted on the distal end of said shaft, a non-elastomeric balloon 3 having its proximal and distal ends affixed to the shaft. See FIGS. 1A and 1B. The attachment can be by conventional proximal and distal banding of balloon material to the central shaft or by bonding of the extruded balloon material to the shaft. The balloon, when deflated, has the appearance of a thin plastic structure wrapped about the distal end of the shaft, adding little thickness to the central shaft. The balloon, when inflated, has an outer surface or topography that is not different from standard angioplasty balloons except for one or more entry 5 and exit 6 ports on each end of the balloon that define the entrance and exit of the one or more of the blood flow channels 7. See FIGS. 2 and 10. A guidewire 4 preferably passes through the channel. See FIG. 1A or C. When inflated within a blood vessel, the one or more channels 7 allow blood to flow past and through the balloon while the force of the balloon as usual dilates the vessel wall and any atheromatous components thereon.

Figure 2A:
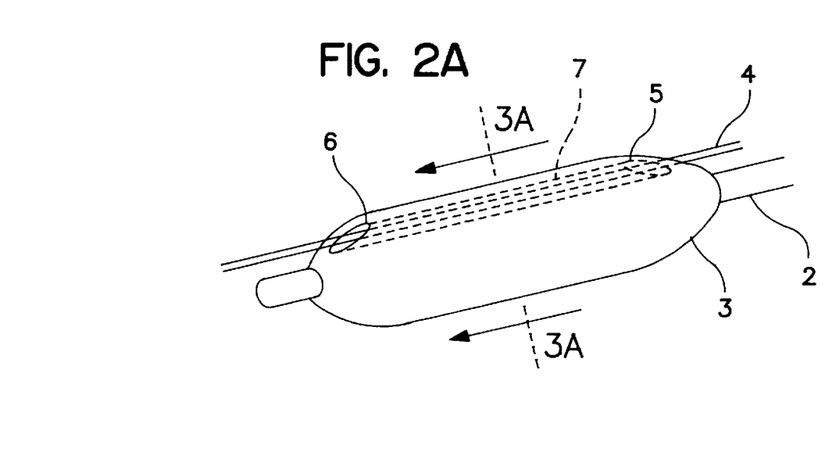
Figure 2B:
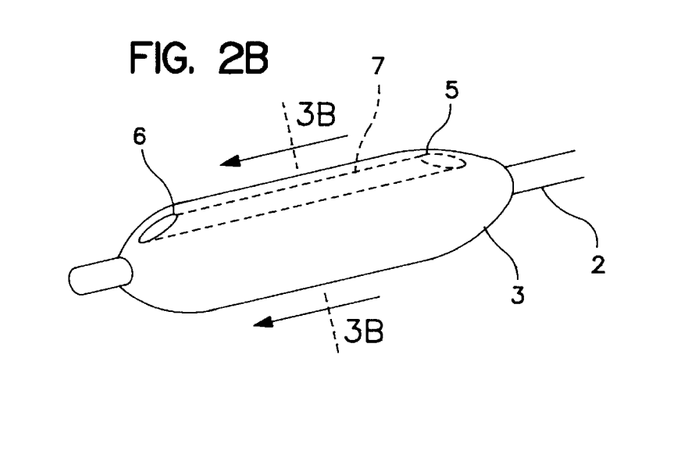
Figure 3A:
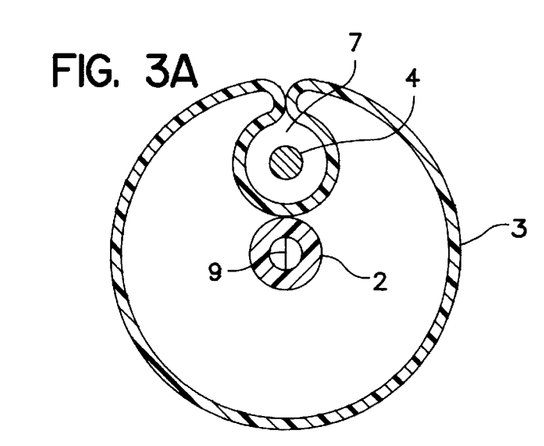
Figure 3B:
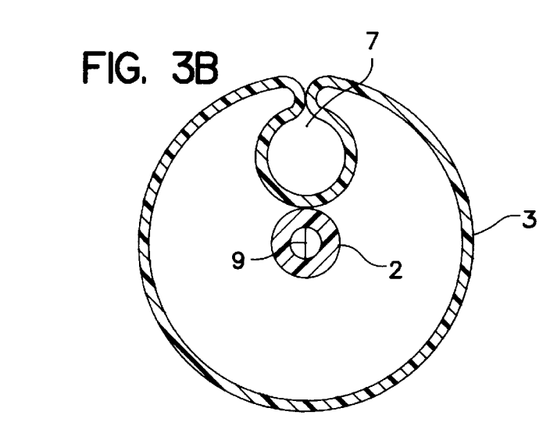
Figure 4A:
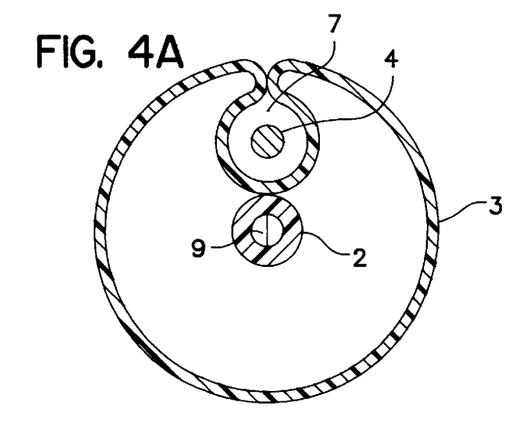
Figure 4B:
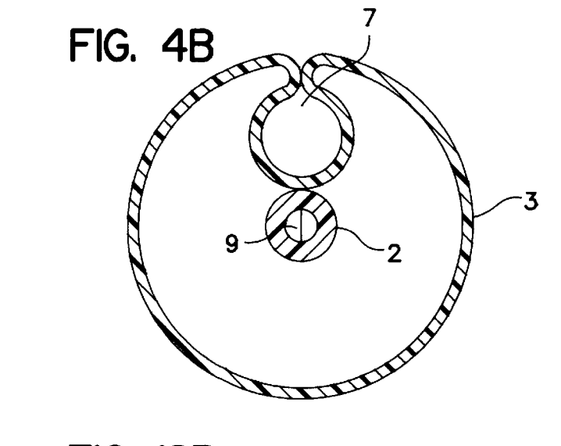
Figure 10A:
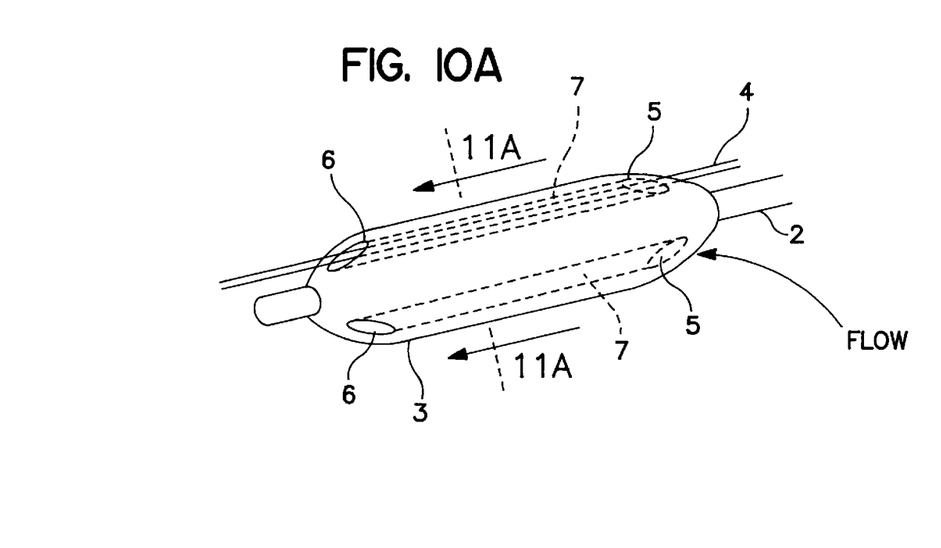
Figure 10B:
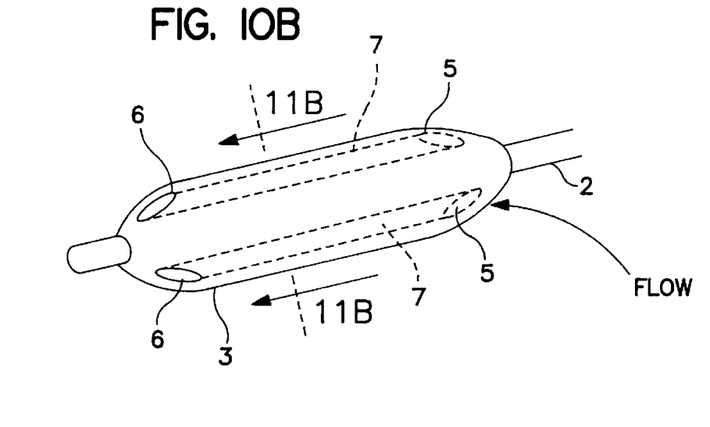
Figure 11A:
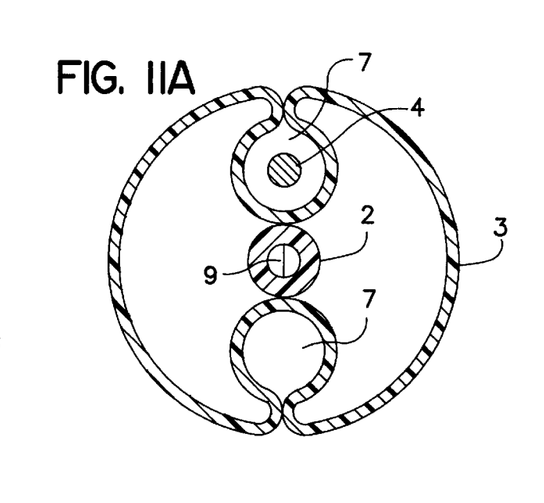
Figure 11B:
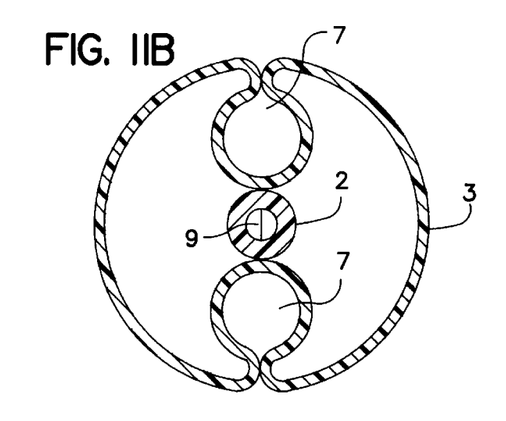
Figure 12A:
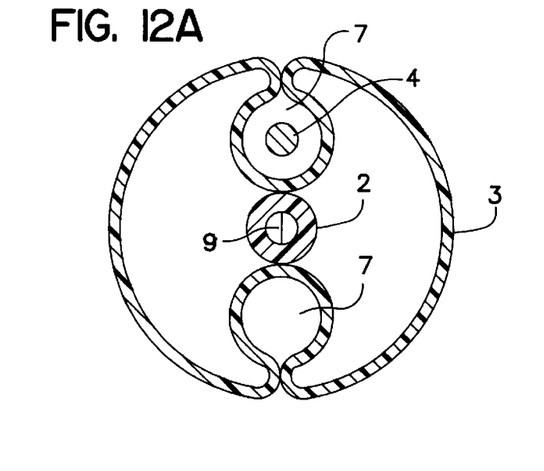
Figure 12B:
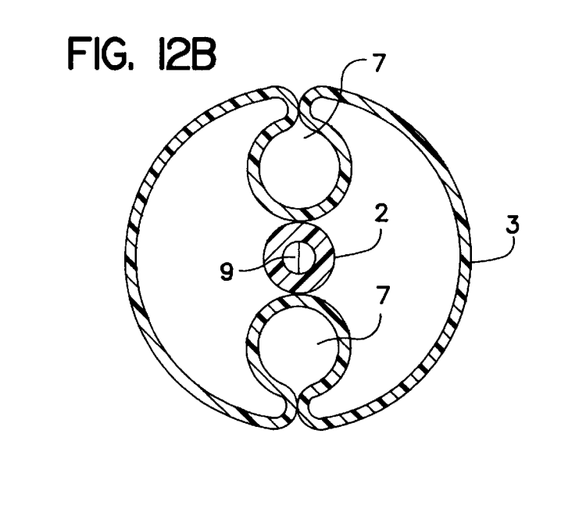

In one embodiment, the inflated balloon structure comprises a single asymmetrically located channel 7 (when viewed in cross section, e.g., FIGS. 3–9) through the length of the balloon, extending from the proximal to the distal end of said balloon. The channel is such that it traverses the length of the balloon longitudinally as shown in FIGS. 1, 2 and 10.

The channel is preferably comprised of balloon material and is designed such that when inflated, the channel preferably becomes circular or substantially circular in cross section and therefore resists the tendency for the channel to collapse radially inward. This channel can be formed close to the central shaft of the catheter as shown in FIGS. 3, 6, 11 and 14 (i.e., a short radial distance from the central shaft) or it can be placed 0.5 to 1.0 mm or more in radial distance from the central shaft as shown cross-sectionally in FIGS. 4, 5, 7 and 8. There is in a preferred aspect of the invention, e.g., a wall comprised of balloon material between the interior of the flow channel(s) and the central catheter shaft.

In another embodiment, the balloon comprises more than one interior channel. Two channels, for example, could be placed 180° apart; or they could be placed 60° apart, e.g., for flow through only one side of the balloon. The embodiment in which the channels are formed 180° apart is shown in cross section in FIGS. 11–16.

FIGS. 10–16 illustrate cross sections of catheter designs having two channels adjacent to the shaft (FIGS. 11 and 14) and removed therefrom (FIGS. 12, 13, 15 and 16), with (Figures "A") and without (Figures "B") guidewire 4.

In another embodiment, the channel(s) could be helical in path of delivery of blood through the balloon from the proximal to the distal end.

In a preferred aspect, a guidewire is placed through the balloon channel, or through one of the balloon channels when multiple channels are included (e.g., 2–4 channels). Such configurations provide a rapid exchange system having the advantages described above, among others, for insertion and removal of the catheter along the wire. When one or more additional channels are also provided, they can serve as perfusion ducts when the balloon is inflated, thus providing a preferred catheter which enables both rapid exchange and additional perfusion (over and above any perfusion provided through the wire-containing first channel).

In a most preferred version of the catheter, a stent is mounted on its end for delivery to a stenosis in a blood vessel. Preferably, such an embodiment is configured with the rapid exchange catheter and, most preferably, with the combined rapid exchange/perfusion catheter. To avoid unnecessarily increasing catheter profile of the uninflated configuration due to existence of the wire in the internal channel (thus restricting access to narrower vessels), the catheter shaft preferably contains a longitudinal groove or recess 14 (preferably, but not necessarily, only through the length of the balloon) to receive the wire in the deflated state as shown in cross section in FIG. 9B. See FIG. 9A for the inflated state of this embodiment. Alternatively, the conventional catheter shaft along the length of the balloon could be replaced by a single solid wire 15 since the guidewire passing through the channel provides supplemental support. See FIG. 9C. In this embodiment, the conventional lumen-containing catheter shaft extends far enough into the balloon for supply of inflation fluid. Connection of the solid wire thereafter to the conventional shaft is by any conventional bonding means, e.g., adhesives, mechanical attachment, etc. or the shaft and thin wire or rod can be unitary, e.g., by conventional molding, extrusion, etc.

Alternatively, a central shaft can be used to provide a lumen for delivery of medications distal to the balloon, e.g., in case of delivery of an agent such as nitroglycerin should an arterial spasm occur. Such a shaft, however, can have a lower profile than conventional shafts.

The use of the catheter of this invention for deployment of a stent is especially advantageous because it enables an even, symmetrical apposition of the stent to the vessel to be achieved, thus preventing acute closure and long-term restenosis.

In yet another embodiment, the channel(s) formed within the balloon are scaffolded or reinforced, e.g., by an additional member to aid in resisting the radial forces tending to cause inward collapse of the flow channels when the balloon is in its inflated state. This scaffolding could be accomplished, for example, by using balloon material of a greater cross-sectional thickness 10, e.g., >0.001 up to about 0.002 or 0.005 inch, these values not being limiting, versus the usual range of about 0.001 inch, in the region of the channel(s), as shown, e.g., in FIGS. 6 and 14. Once the balloon is formed with channels having regionally thickened balloon material disposed about their circumference, they will have far greater resistance to radial forces tending to promote collapse and yet maintain enough flexibility to assume a low profile in the deflated state.

Figure 5A:
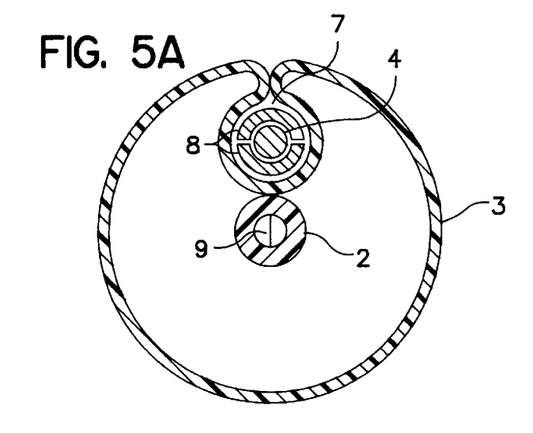
Figure 5B:
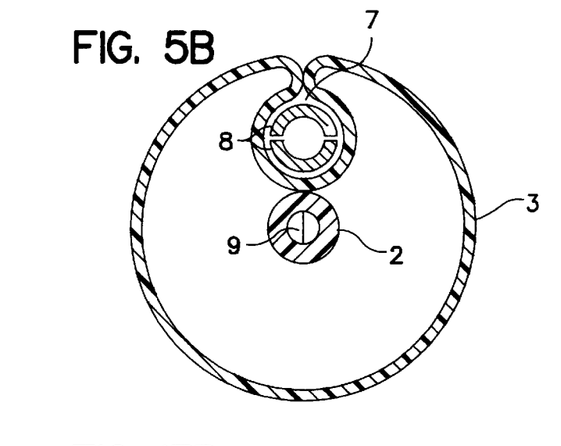
Figure 6A:
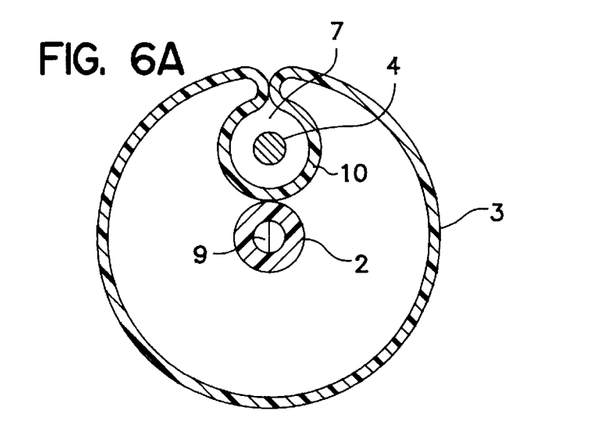
Figure 6B:
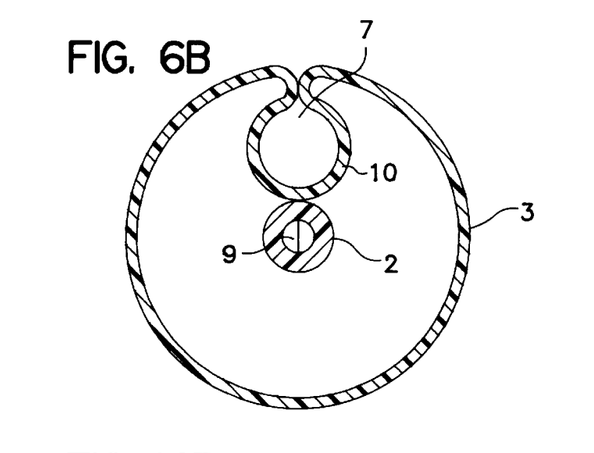
Figure 13A:
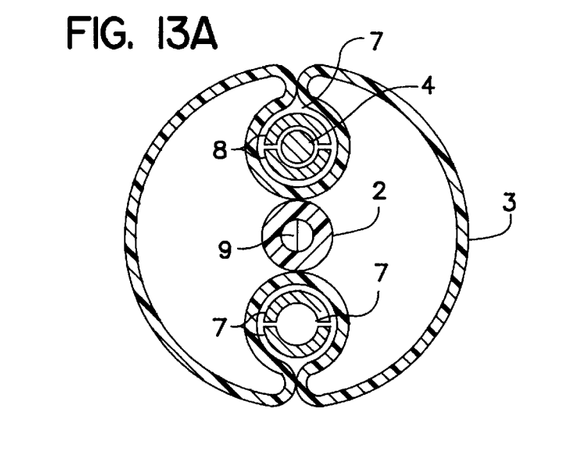
Figure 13B:
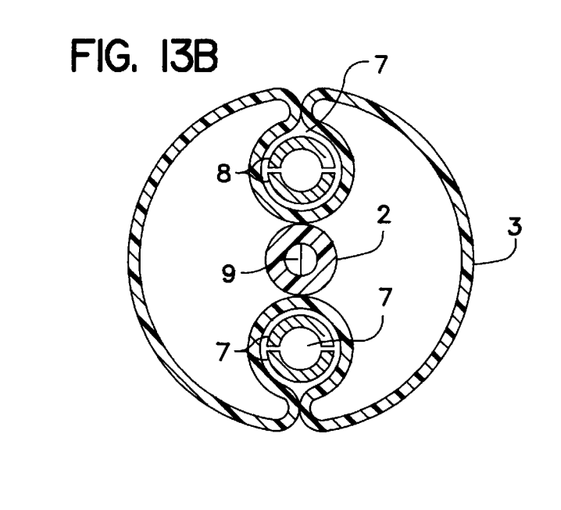
Figure 14A:
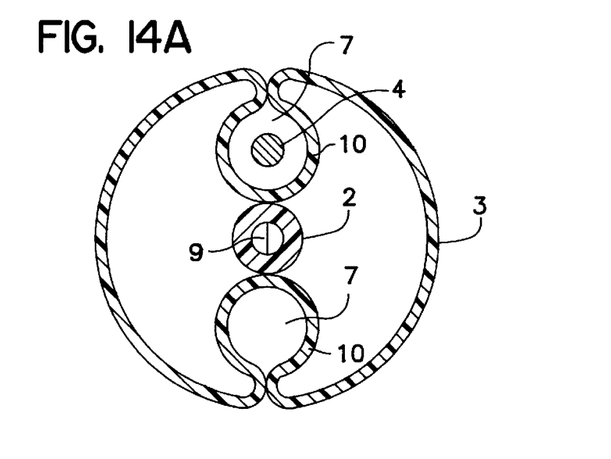
Figure 14B:
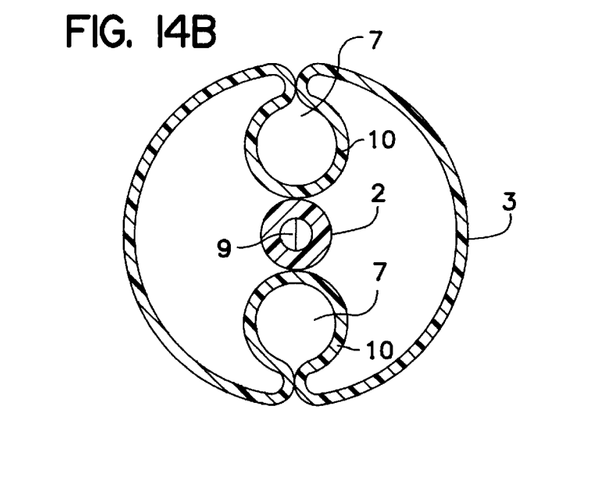

An additional version of this embodiment is one in which scaffolding of each channel is accomplished by the addition of a long cylindrical member within the channel placed either during manufacturing or thereafter. This cylinder member is a tubular insert having the shape of the channel. In one embodiment, the cylindrical member or tubular insert is divided into two pieces along its length, e.g., comprises two hemi-cylinders 8. The material of these whole cylinders and hemi-cylinders (e.g., from the same classes of materials used to form balloons, including the same materials used for balloons) preferably will have flexible properties to allow for their collapse while in the deflated state but will provide sufficient rigidity in the inflated state to resist any inwardly directed radial forces caused by the high inflation pressures used in standard balloon techniques. In the inflated state, these hemi-cylinders would form a single cylinder within each channel and assist in the maintenance of flow for the perfusion catheter, as shown in FIGS. 5 and 13. As a result, like all other embodiments disclosed herein, the balloon will be collapsible to minimize profile when deflated and will be rigid when inflated.

The single or hemi cylinder reinforcement embodiments may extend a length less than, equal to or greater than the channel length in all devices of this invention. When the cylinders extend beyond the ends of the channels (e.g., for a few centimeters along the central shaft and optionally attached to the shaft), the wire in the rapid exchange device can more easily be inserted. See FIG. 1C.

Figure 7A:
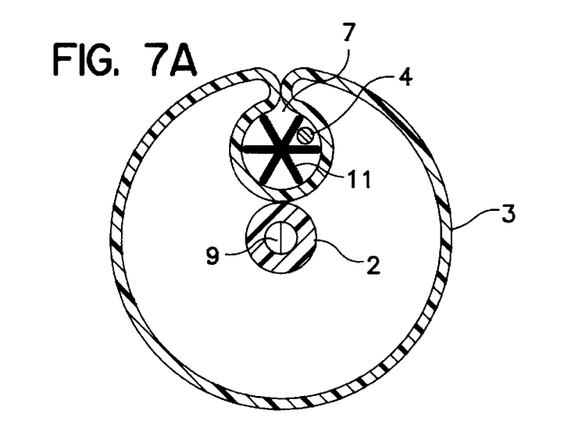
Figure 7B:
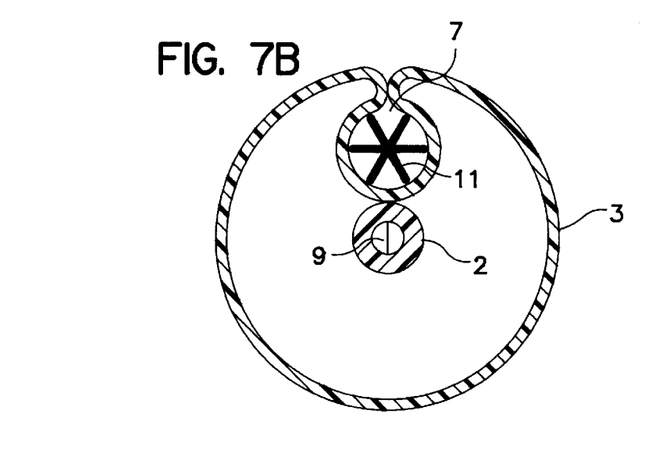
Figure 8A:
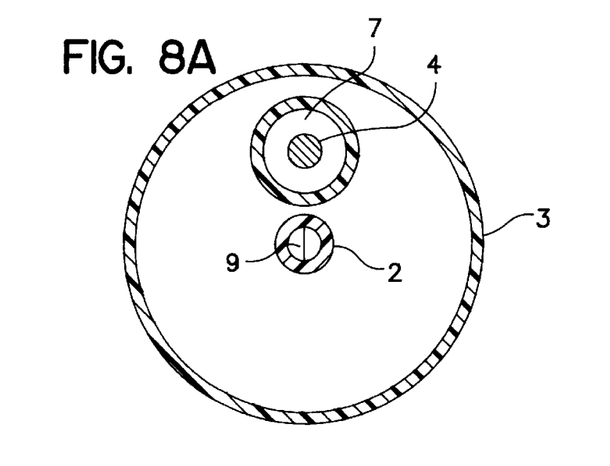
Figure 8B:
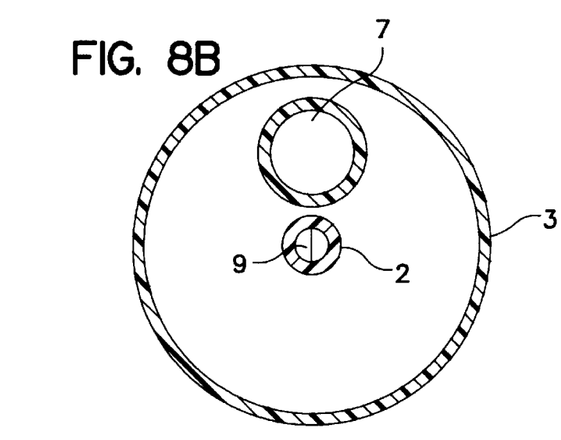
Figure 9A:
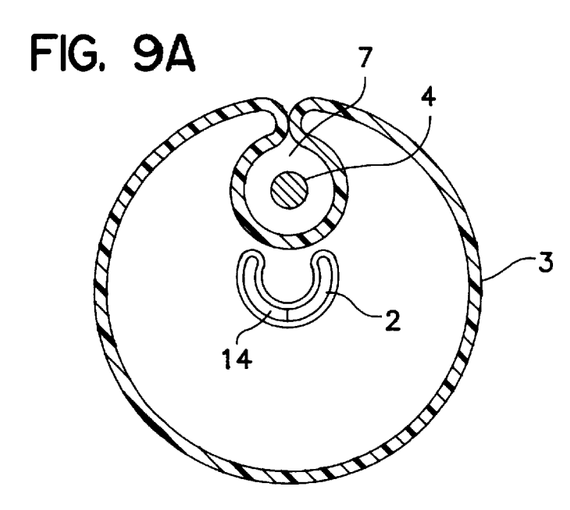
Figure 9B:
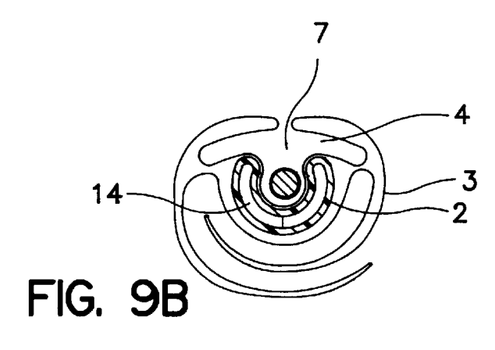
Figure 9C:
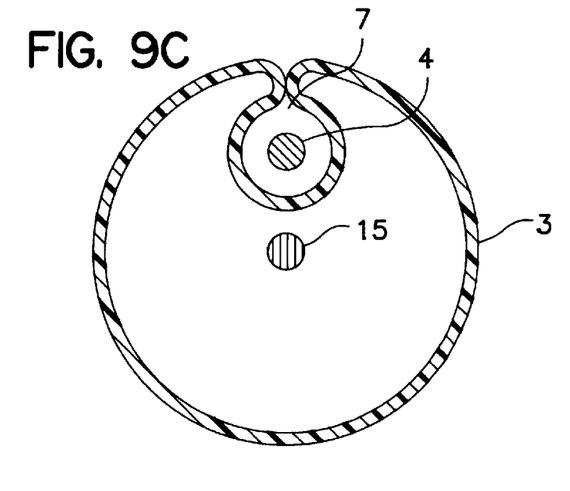
Figure 15A:
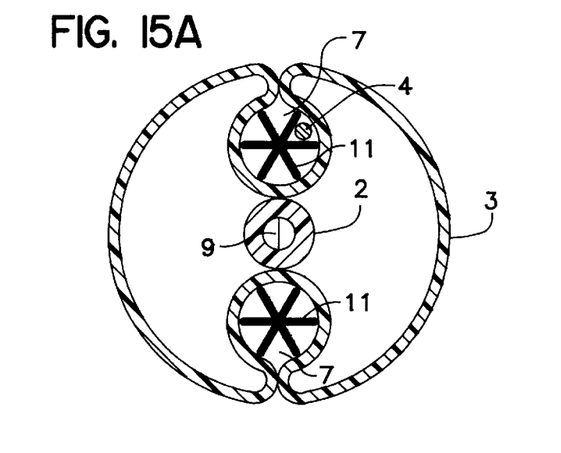
Figure 15B:
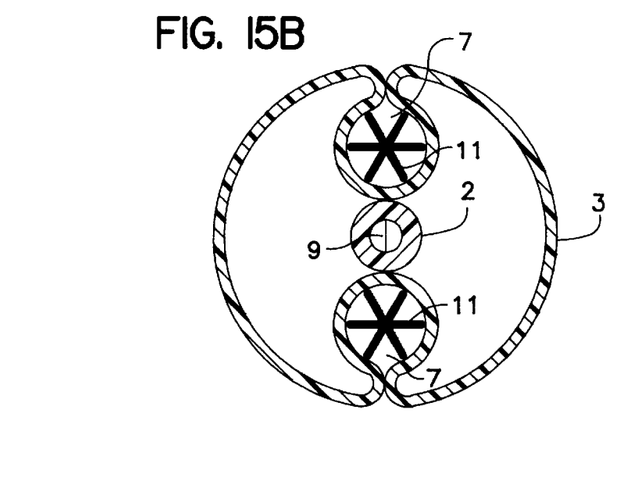
Figure 16A:
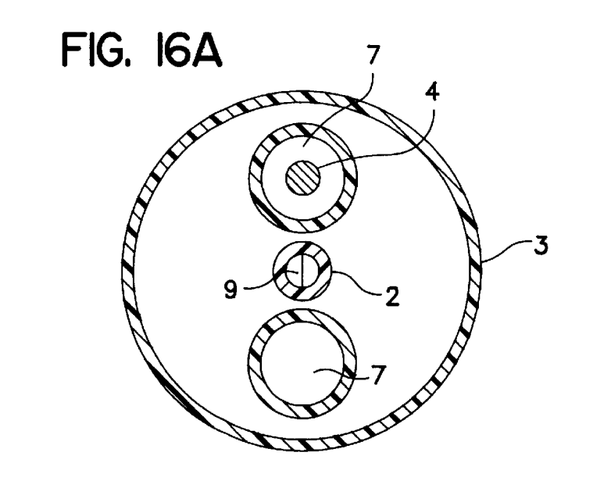
Figure 16B:
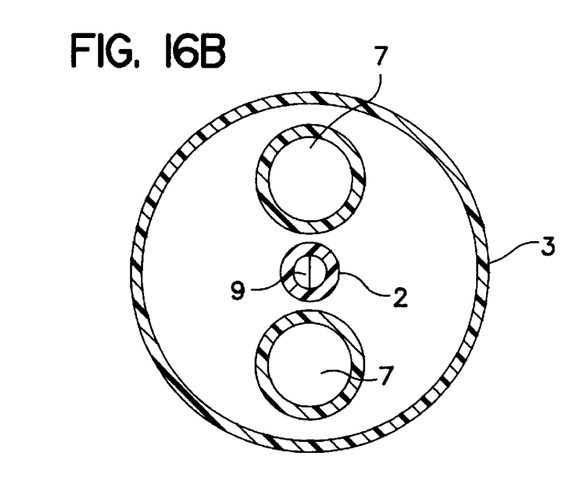
Figure 18A:
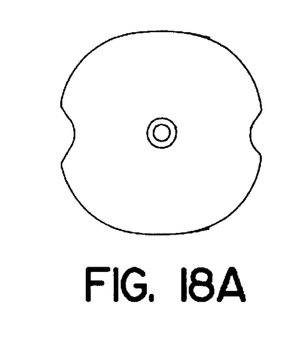
Figure 18B:
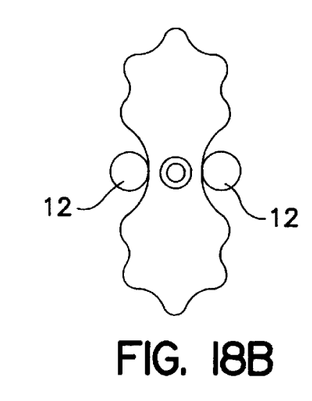
Figure 18C:
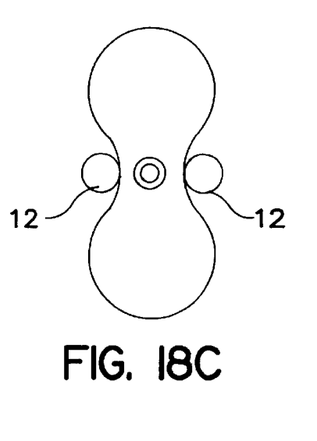
Figure 18D:
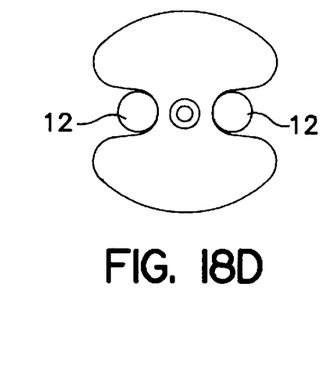
Figure 18E:
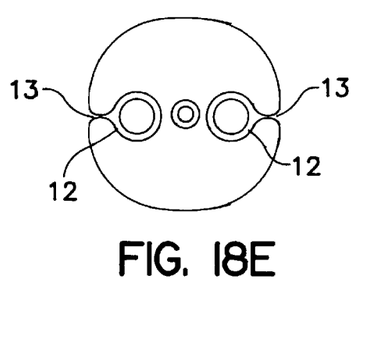

Other types of scaffolding are also useful, such as a series of longitudinal supports 11 shown in cross section in FIGS. 7 and 15 where six such supports are shown, more or fewer also being possible.

All of the embodiments of this invention allow for modifications in the amount of blood flow by varying the size (e.g., length, diameter), configuration (e.g., cross sectional shape (circular, elliptical, triangular), helical (slower) versus linear longitudinal (faster), etc.) and/or number of flow channels selected. Typically, the channel diameter will be in the range of about 0.5 to about 1 mm, lesser or greater values being possible, and the cross sectional shape will be substantially circular, especially in the case of perfusion. The inflation and flow characteristics can also be affected by the choice of balloon material. For a given material, the higher the inflation pressure, the more likely it is that the channels will be affected by inward radial compression forces. The softer or more compliant the balloon material, the less open will be a given balloon's flow channel at a given inflation pressure.

The preferred perfusion-only embodiments will have at least two lumens 9 traversing the central catheter shaft, as shown in FIGS. 3–8 and 11–16. Three or even more lumens can also be included in the catheter shaft. One lumen can be for the purpose of guidewire use, for delivery of agents downstream of the device and/or for sample withdrawal when the guidewire is removed. The other inner lumen of the catheter shaft is contiguous with the balloon lumen and is for the purpose of inflating and deflating the balloon. Of course, for the perfusion/rapid exchange embodiment, if desired, the shaft can have only a single lumen, as discussed above.

The formation of the balloon, with its flow channels described herein, can be accomplished in several ways, preferably by molding and/or extrusion techniques. The method illustrated in FIG. 18 involves a modification of a molding process commonly used in the manufacture of conventional balloons. For example, prior to the molding process, both the proximal and distal ends of the balloon are typically affixed to the catheter shaft. The balloon has excess material about the site(s) where one or more channels are to be formed. The excess material will correspond to the surface(s) shown interior to the balloons of FIGS. 3–7, 9 and 11–15, i.e., will be sufficient to permit formation of the inner channels. When the channel material is desired to be thicker than usual, this can be accomplished by using thicker material in this region of the excess material. This can be accomplished in several ways. In a preferred aspect, the balloon material is extended (prior to bonding to the shaft) with thickened walls in the regions where one desires a channel. The amounts of excess balloon material and proper thickness can be determined in a given case by routine experimentation. Upon molding, the thicker regions then form the channels. Alternatively, one can simply layer, by bonding techniques, standard longitudinal sections of balloon (or other) material in those regions where one desires thickening and then mold the balloon. This bonded layer not only thickens the regions needed to form the channels but acts also as a scaffolding as well, as discussed above.

Adhesives are conventional, e.g., as currently used to bond the extruded balloon to the shaft. The layers can also be conventionally heat sealed. The channel walls can also comprise materials, other than balloon materials, which are adjoined to the balloon to form the channels. Also, the channel walls can be treated for purposes of increasing strength.

In manufacturing, one or more cylindrical members 12 are placed within a balloon mold in the position of the one or more desired channel(s). See FIG. 18(b)–(e). When inflation of the balloon within the mold takes place, the excess balloon material envelopes the one or more cylindrical members as in FIG. 18(d). (The members can be pre-attached to the mold.) During or after the molding process, the contiguous balloon material will be conventionally heat sealed along line 13 to form the channel(s) or otherwise sealed, e.g., using adhesives. See FIG. 18(e). For instance, once the balloon molding is completed, the mold is separated, the cylindrical members 12 used to support the flow channels during molding are removed, and the initially excess balloon material that has now formed into channel(s) and comprises the outermost portion of said channel, is bonded together, e.g., at 13, using the mentioned conventional techniques to complete its circumference. See FIG. 18(e). It is also possible to employ movable cylindrical members which are moved toward each other during the molding process to facilitate achievement of the final configuration of FIG. 18(e).

In another method of manufacture, the balloon and its one or more channels are extruded using conventional plastic extrusion technology. The one or more interior channels are achieved by extrusion of one or more cylinders (having walls of a desired thickness) within the larger cylinder that is the balloon. See FIGS. 8 and 16. In one method, the inner channel is extruded at the same time as the exterior balloon in a single process. Alternatively, the channel(s) can be extruded separately and then added to the interior of the larger, exterior balloon at the time of assembly by sealing, e.g., using adhesives or heat sealing and cutting away the openings to the channel(s).

The addition of any needed scaffolding in any manufacturing method can be accomplished once the channelled balloon is disposed about the distal end of the catheter. Suitable materials for any scaffolding include high or low density polyethylene (or other standard balloon material) or any other similar material. They can be metallic or even elastomeric like a rubber substance. They are all routinely preparable, e.g., by routine extrusion or molding. The nature of the optional reinforcement effective to enhance flow through a channel of this invention will be determined by routine experimentation. When a channel is simply used to achieve rapid exchange, i.e., movement of the balloon over a guidewire, the degree of scaffolding/reinforcement can be less.

In all embodiments, the mentioned advantages over conventional angioplasty balloon catheters are realized. Because of the emergence of vascular stents in the management of coronary stenoses, there remains a very large need for catheters able to uniformly deploy them, especially in rapid exchange systems. This invention achieves these ends uniquely well. Despite the advent of heavy stent usage, there remains a need for use of perfusion balloons, e.g., in situations of dissection, a tear in the arterial wall that is a common complication of standard angioplasty. The channels of this invention maximize the flow rate when compared with existing perfusion technology. Flow rates with this device should reach near normal when used in the coronary bed (80 to 100 ml/min), since flow is not limited by use of the central catheter shaft.

The triple combination of stent deployment/rapid exchange/perfusion offered by this invention is unique. The fact that the channels of the present invention have only "potential" space when the device is in its deflated state, allows the latter to have a much lower profile and gives it the ability to reach lesions in smaller blood vessels that were not previously reachable with current technology. The larger flow channels in this invention also decrease the likelihood of thrombosis within the device, another potential complication.

Features of the catheter and balloon of this invention not discussed herein are conventional, including sizes, materials, dimensions, tolerances, design options, methods of manufacturing and use, etc. and can be adapted to this invention using at most routine experimentation. Especially preferred for use with this invention are conventional methods and devices for applying radioactivity for the purposes discussed above. In a special embodiment of this invention, when a solid metal wire replaces the conventional shaft through the balloon segment, this wire can be made radioactive using conventional techniques.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein: in each figure the "A" version being with rapid exchange (wire in channel) and the "B" version being without, e.g., for perfusion;

FIG. 1 shows overviews of balloon catheters;

FIGS. 2 and 10 show overviews of the balloons of this invention mounted on a catheter shaft and having one (FIG. 2) or two (FIG. 10) channels;

FIGS. 3–9 and 11–16 show cross sections of perfusion catheter of the invention with one (FIGS. 3–9) or two channels (FIGS. 11–16) optionally, with supporting scaffolding (FIGS. 5–7 and 13–15) or a shaft groove (FIG. 9); and FIG. 18 shows a method of manufacture of a catheter of this invention.

Without further elaboration, it is believed that one skilled in the art can, using the preceding description, utilize the present invention to its fullest extent. The preferred specific embodiments are, therefore, to be construed as merely illustrative, and not limitative of the remainder of the disclosure in any way whatsoever.

The entire disclosure of all applications, patents and publications, cited above, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions. The preceding can be repeated with similar success by substituting the generically or specifically described operating conditions of this invention for those used therein.

What is claimed is:

1. A perfusion balloon catheter useful for angioplasty, comprising, a catheter shaft having an outer surface, and concentrically mounted on and encircling said shaft, an inflatable dilation balloon useful for angioplasty, the balloon having a longitudinal axis and comprising:

an inflatable space defined by an outer closed surface of the balloon which contacts an inner surface of a blood vessel when said balloon is inflated in said blood vessel, and said balloon having distal and proximal ends proximate said catheter shaft, said balloon when inflated having an interior with at least one laterally offset walled inner channel formed in its interior and disposed between said outer surface of said shaft, which inner channel extends from and terminates at said proximal and distal ends, said inner channel comprising a wall defining a closed surface which is distinct from the surface of said shaft and which is laterally displaced from the axis of the balloon so as to have a portion closes to said balloon outer surface and a portion closes to said shaft, said portion closest to said balloon outer surface adjoining said balloon outer surface along a line extending from said balloon proximal end to said distal end, whereby when said balloon is inflated in a blood vessel and said outer surface is in contact with the inner surface of said blood vessel, blood flows through said inner channel from the proximal to the distal end of said balloon.

2. A perfusion balloon catheter of claim 1 wherein the portion of said inner channel wall closest to said outer surface of said balloon adjoins said balloon outer surface along a line from said balloon proximal end to said distal end.

3. A perfusion balloon catheter of claim 1 wherein said inner channel is continuously sealed along said line.

4. A perfusion balloon catheter of claim 3 wherein the portion of said inner channel closest to said shaft adjoins said shaft.

5. A perfusion balloon catheter of claim 3 wherein the portion closest to said shaft is spaced apart from said shaft, whereby when said balloon is inflated by an inflation medium, said medium is positioned between said shaft and said inner channel wall.

6. A perfusion balloon catheter of claim 3 having two of said inner channels.

7. A perfusion balloon catheter of claim 3 wherein said inner channel has a wall which is thicker than said outer balloon surface.

8. A perfusion balloon catheter of claim 3 wherein said inner channel wall is reinforced by a tubular insert having the shape of said channel.

9. A perfusion balloon catheter of claim 8 wherein said tubular insert comprises two hemi-cylinders.

10. A perfusion balloon catheter of claim 3 further comprising a second channel passing through its interior from its proximal to its distal end and a guidewire passing through said second channel from said proximal to said distal end.

11. A perfusion balloon catheter useful for angioplasty comprising a center annular shaft and, mounted thereon, and encircling inflatable balloon surface having a proximal and distal end, and an inner channel in the balloon surface and located between said balloon surface and said shaft, said channel being defined by a surface which is laterally separated from and distinct from both said shaft and said balloon surface and said channel having open ends at the proximal and distal ends of the balloon.

12. A balloon catheter useful for angioplasty comprising:

an angioplasty balloon having an interior space, an axis, a proximal end and a distal end, the balloon further having an interior channel of a selected shape passing through its interior space, the interior channel having end regions terminating at the proximal and distal ends of the balloon and being laterally offset from the axis of the balloon, a guidewire passing through said interior channel from said proximal to said distal end of the balloon, and a cylinder insert comprising two hemi-cylinders disposed in the interior channel to provide scaffolding therein to reinforce at least the end regions of said interior channel, the cylinder insert having especially the shape of said interior channel or comprising interior channel walls which are of thicker balloon material than the surface of said balloon which contact a blood vessel wall when the balloon is inflated.

* * * * *